(12) United States Patent
Murat Hocaoglu et al.

(10) Patent No.: US 11,541,418 B2
(45) Date of Patent: Jan. 3, 2023

(54) CARRIER ELEMENT FOR WASTEWATER TREATMENT AND CARRIER ELEMENT MODIFICATION METHOD

(71) Applicant: TURKIYE BILIMSEL VE TEKNOLOJIK ARASTIRMA KURUMU (TUBITAK), Ankara (TR)

(72) Inventors: Selda Murat Hocaoglu, Gebze-Kocaeli (TR); Pamir Talazan, Gebze-Kocaeli (TR); Recep Partal, Gebze-Kocaeli (TR); Irfan Basturk, Gebze-Koceali (TR)

(73) Assignee: TURKIYE BILIMSEL VE TEKNOLOJIK ARASTIRMA KURUMU (TUBITAK), Ankara (TR)

( * ) Notice: Subject to any disclaimer, the term of this patent is extended or adjusted under 35 U.S.C. 154(b) by 164 days.

(21) Appl. No.: 17/130,899

(22) Filed: Dec. 22, 2020

(65) Prior Publication Data
US 2021/0188675 A1    Jun. 24, 2021

(30) Foreign Application Priority Data
Dec. 23, 2019    (TR) ................... 2019/21186

(51) Int. Cl.
    *B05D 1/18*    (2006.01)
(52) U.S. Cl.
    CPC ..................... *B05D 1/18* (2013.01)

(58) Field of Classification Search
    CPC ....................................................... B05D 1/18
    See application file for complete search history.

(56) References Cited

U.S. PATENT DOCUMENTS

| | | | |
|---|---|---|---|
| 5,543,039 A * | 8/1996 | Odegaard | C02F 3/10 261/95 |
| 5,783,069 A | 7/1998 | Frank | |
| 7,189,323 B2 | 3/2007 | Lofqvist et al. | |
| 2012/0037551 A1 | 2/2012 | Kenyeres et al. | |
| 2016/0376175 A1 | 12/2016 | Welander et al. | |

FOREIGN PATENT DOCUMENTS

| | | |
|---|---|---|
| CN | 203715362 U | 7/2014 |
| EP | 0142123 A2 | 5/1985 |
| EP | 0750591 | 1/1997 |
| WO | WO 95/25072 | 9/1995 |
| WO | WO 2017/144928 A1 | 8/2017 |

OTHER PUBLICATIONS

Lu et al., "Polyolefin Wax Modification Improved Characteristics of Nutrient Release from Biopolymer-Coated Phosphorus Fertilizers" (2019) (Year: 2019).*

(Continued)

*Primary Examiner* — Nathan T Leong
(74) *Attorney, Agent, or Firm* — Crose Law LLC; Bradley D. Crose

(57) ABSTRACT

The invention relates to the development of a carrier material providing high surface area for biofilm formation in wastewater treatment plants and a carrier material surface modification method for accelerating and enriching biofilm formation.

6 Claims, 3 Drawing Sheets

(56) References Cited

OTHER PUBLICATIONS

Figure 1:
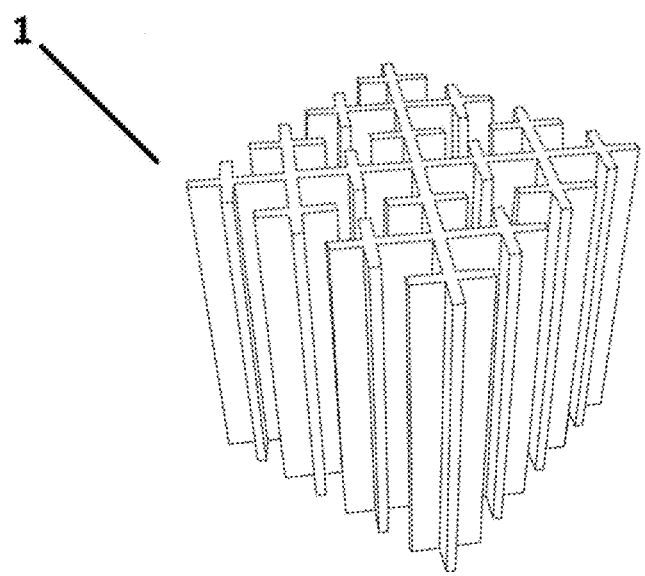

Barwal, A. et al., "Impact of carrier filling ratio on oxygen uptake and transfer rate, volumetric oxygen transfer coefficient and energy saving potential in a lab-scale MBBR" Journal of Water Process Engineering, vol. 8, dated (2015), pp 202-208.
Busscher, H. J. et al., Initial microbial adhesion is a determinant for the strength of biofilm adhesion. FEMS Microbiology Letters, 128(3), dated (1995), 229-234.
Cerca, N. et al., "Quantitative analysis of adhesion and biofilm formation on hydrophilic and hydrophobic surfaces of clinical isolates of *Staphylococcus epidermidis*" Res. Microbiol., 156, (2005), 506-514.
Donlan, R. M. (2002). Biofilms: microbial life on surfaces. Emerging Infectious Diseases 8(9), (2002), pp. 881-890.
Garcia, Kody, "The Effect of Biofilm Carrier Length on Nitrification in Moving Bed Biofilm Reactors: An Examination of Mixing Intensity, Shock Loadings, and pH Changes" (2016).
Gu, Q. et al., "Influence of carrier filling ratio on the performance of moving bed biofilm reactor in treating coking wastewater. Bioresource Technology," 166, dated (2014) pp. 72-78.
Harmsen, M. et al., "An update on *Pseudomonas aeruginosa* biofilm formation, tolerance, and dispersal" FEMS Immunology and Medical Microbiology 59, dated (2010), pp. 253-268.
Hu, H. et al., (2017). A strategy to speed up formation, and strengthen activity of biofilms at low temperature. RSC Advances, 7(37), (2.017), p. 22788-22796.
Huang, C.et al. "Comparison of biomass from integrated fixed-film activated sludge (IFAS), moving bed biofilm reactor (MBBR) and membrane bioreactor (MBR) treating recalcitrant organics: Importance of attached biomass" J. Hazard. Mater., 326, (2017), pp. 120-129.
Jing. J. Y. et al. "Carrier effects on oxygen mass transfer behavior in a moving-bed biofilm reactor. Asia-Pacific Journal of Chemical Engineering", 4( 5), (2009), pp. 618-623.
Mannina, G. et al., "Bacterial community structure and removal performances in IFAS-MBRs: A pilot plant case study" J. Environ. Manage., 198, (2017), pp. 122-131.
Mao, Y. et al., (2017). Accelerated startup of moving bed biofilm process with novel electrophilic suspended biofilm carriers. Chemical Engineering Journal, 315, (2017), pp. 364-372.
Mazumder, S. et al., "Role of hydrophobicity in bacterial adherence to carbon nanostructures and biofilm formation" J. Bioadhesion Biofilm Res., 26, (3):, (2010), pp. 333-339.
Pagedar, A. et al., "*Staphylococcus aureus* biofilms and temperature influences its survival in preformed biofilms Introduction" S98 J. Basic Microbiol., 50, (2010), pp. 98-106.
Piculell, Maria "New Dimensions of Moving Bed Biofilm Carriers: Influence of biofilm thickness and control possibilities", Lund: Department of Chemical Engineering, Lund University, dated (2016).
Rosenberg, M. et al., "Hydrophobic interactions in bacterial adhesion. Advances in Microbial Ecology 9", (1986), pp. 353-393.
Thomas, W. E. et al., "Shear-dependent 'stick-and-roll' adhesion of type 1 fimbriated *Escherichia coli*" Molecular Microbiology 53, (2004) pp. 1545-1557.
Young, B. et al., "Low temperature MBBR nitrification: Microbiome analysis" Water Res., 111, (2017), pp. 224-233.

\* cited by examiner

CARRIER ELEMENT FOR WASTEWATER TREATMENT AND CARRIER ELEMENT MODIFICATION METHOD

CROSS-REFERENCE TO RELATED APPLICATION

The present application claims the benefit of priority of Turkish Patent Application No. TR 2019/21186, filed on Dec. 23, 2019, the content of which is incorporated herein by reference in its entirety for all purposes.

TECHNICAL FIELD

This invention relates to the development of a carrier element providing high surface area for biofilm formation in wastewater treatment plants and a carrier element surface modification method for accelerating and enriching biofilm formation. The carrier element developed within the scope of the invention has three forms: cubic, cylindrical and second-stage plate-type cylindrical forms. The invention covers the modified and unmodified states of the surfaces of each of these three forms and the method related to this modification.

BACKGROUND

Wastewater cannot be discharged to receiving environments like rivers, lakes or seas without being treated due to its high content of organic matter, nutrients and micropollutants. Most of the domestic and industrial wastewater is mainly treated with biological treatment processes using microorganisms. The biological treatment process to be used depends on the wastewater characteristics, the quality of the water to be discharged and the environmental conditions. Treatment efficiency is affected by the number and residence time of the microorganisms retained in the reactor. With the increase in the number of active microorganisms, the treatment efficiency increases and the reactor volume decreases. A major part of the current biological treatment systems comprises conventional active sludge systems where microorganisms grow in suspension. In these systems, microorganisms move freely in flocs, and the pollutants in water are broken down by the microorganisms in aerobic or anaerobic environments. At the next step, microorganisms are separated from the water phase and so, the biological treatment phase is completed. In these systems, in order to keep the biomass concentration at a certain level, the microorganisms separated at sedimentation phase are sent back to the biological reactor to a large extent. As a result, surface areas of sedimentation tanks get large, and a significant hydraulic capacity is used for the return activated sludge. Another treatment method using microorganisms is, biofilm systems where microorganisms proliferate by attaching to a surface inside the reactor, which provides advantage in the separation of water phase and biomass and allows the retention of the biomass in the reactor to a large extent. Biofilm is a complex community of bacterial cells attaching to each other and to a surface. Extracellular polymeric substances (EPS) produced by microorganisms play an active role in attachment. EPSs in a biofilm serve as a kind of protective barrier against external effects for microorganisms in the biofilm and this allows the bacterial community, living in the biofilm, to be more resistant to toxic pollutants. Microbial extracellular polymeric substances are composed of molecules with high molecular weight such as polysaccharides, DNA, proteins, lipids and humic acids (Flemming & Wingender, 2010). EPSs secreted by microorganisms play a role in attachment to surface, which is the first step of biofilm formation, and subsequently in colony formation, and also affect the structure and stability of the microbial community. EPS formation and composition are affected by many factors such as wastewater characteristics (carbon/nitrogen ratio, pH, ionic strength, toxic substance concentration, etc.) and reactor operating conditions (sludge age and hydraulic retention time, dissolved oxygen concentration and shearing forces).

Conventional biofilm systems include trickling filters in which stone and large block materials are used as surfaces on a fixed bed. Even though these systems have various advantages specific to biofilm systems, due to some disadvantages like clogging over time due to particles and/or biofilm formation in wastewater, dead space formation, efficiency loss and limited application capacity, they have not been commonly used. However, in the last two decades, along with the development of plastic carrier elements, moving bed biofilm treatment systems, combining the advantages of suspension and biofilm systems, have started to become widespread. Moving bed biofilm reactors are basically composed of a diffuser system to meet the oxygen need in the biological reactor and to make a mixture, a mechanical mixer for use in case of treatment under anoxic conditions and/or anaerobic conditions, carrier elements and a sieve to keep carrier elements in the reactor. In moving bed biofilm treatment systems, the carrier element used as surface for biofilm development is suspended and in motion in the reactor. So, problems such as clogging, dead spaces and decrease of treatment efficiency encountered in conventional biofilm systems such as trickling filters are eliminated. Moving bed biofilm systems allow the coexistence of biofilms and microorganisms growing in suspension, and the amount of biomass retained in the reactor can be increased. Thus, both the reactor volume and the dimensions of the sedimentation tanks can be smaller. Compared to conventional activated sludge systems, biofilm systems have the advantages of high tolerance to shock loads and load fluctuations, high adaptability to low temperatures, strength against toxic pollutants and application of high loads in smaller volumes. However, due to the facts that biofilm attachment to carrier element surface and colony formation take a long time, that the first biofilm formation can be fragile, and therefore, it can come apart as a whole negatively affect the start-up period of biofilm systems, and it may take too long for the system to stabilize and reach steady state conditions. Especially, some studies indicate that the start-up period in which biofilm attachment and colony formation take place at low temperatures, can take up to half a year (Hu, He, Yu, Liu, & Zhang, 2017).

In wastewater treatment plants, carrier elements can be employed both as fixed beds in anaerobic treatment systems and as the basic elements of treatment technologies with moving bed biofilm systems such as MBBR (mixed bed biofilm reactor) and IFAS (integrated fixed-film activated sludge); and they can be used to increase the capacities of existing biological wastewater treatment plants. In moving bed systems, to create a high surface area, generally 40-60% of the biological reactor volume is filled with carrier element (Huang et al., 2017; Mannina et al., 2017; Young et al., 2017) and a period of time is waited for biofilm formation after adding inoculum sludge. There are studies in the literature about the effect of the amount of carrier element and its ratio in total volume, on treatment performance and material transfer. These studies report that the carrier element ratio in the reactor has a positive effect on performance and oxygen transfer, up to an optimum value, and that however as the optimum ratio is exceeded, the mixing conditions in the reactor deteriorate and consequently the oxygen transfer and treatment efficiency are negatively affected (Barwal & Chaudhary, 2015; Jing, Feng, & Li, 2009; Gu, Sun, Wu, Li, & Qiu, 2014). Accordingly, the use of carrier elements with high effective specific surface area can both reduce the total amount of carrier element and contribute to the improvement of mixing conditions.

There are many carrier elements developed for use in wastewater treatment and moving bed systems. Some of them are cylindrical carriers (U.S. Pat. No. 5,543,039A), cylindrical carriers with spiral blades (US005783069A), circular carriers with very low carrier height and diameter ratio or honeycomb-form carriers (U.S. Pat. No. 7,189,323 B2), wave-form carriers (US 2016/0376175 A1), carriers made of filament yarns (WO 2017/144928 A1), fiber ball carriers (CN203715362U) and foam coated rubber parts (EP-A-0 142 123). The patent application numbered US 2012/0037551 A1 refers to carriers in cubic form made of textile, and the biofilm growth chambers at the center of these carriers are open only in two directions.

Unlike the cubic-form carrier in the patent numbered US 2012/0037551 A1, the cubic configuration in this invention has interlocking three-way open and three-channel biofilm growth chambers in the center, to support substrate and oxygen transfer.

While some carriers are made up of yarn and fiber, most of the carrier materials used in treatment plants are generally made up of plastic materials like PVC and polyethylene which are economical and whose specific gravities are close to water.

It is known that, due to friction of materials to each other, biofilm attachment on outer surfaces of the carrier element remains limited, and the outer surface cannot be used efficiently. On the contrary, an outer surface designed to be protective against impacts, chambers inside the carrier element and their surfaces provide convenient surfaces for biofilm attachment. The form of the outer surface of the carrier element is also important for the movement of the carrier in water. For instance, the existence of protrusions (fins) and/or recesses, along with the move of air bubbles and water, may help the carrier element make rotational (turning) movements in water, which might make it easier to transfer oxygen, substrate and nutrients into the biofilm. While clogging cases can be reduced owing to the open pores in the carrier element, the interaction of the biofilm attached to surfaces with oxygen and contaminants in the wastewater can be improved. Although the cylindrical-type carrier elements are efficient in terms of treatment performance, the effective specific surface area ($m^2/m^3$) of the existing carriers is limited. By increasing the effective specific surface area of these carriers, the wastewater loading rate can be increased, the amount of carrier element to be used can be reduced, and the mixing conditions can be improved. However, as in the patent document EP0750591, the carrier elements with greatly increased surface areas generally have small dimensions and small gaps in the material and frequently experience clogging problems and dead spaces in biofilm formation. It is possible to experience clogging problem especially in wastewaters containing particles of fiber and cellulose. Another important matter related to the carrier element is the ratio of the effective specific surface area to the total specific surface area. A small ratio means that a significant part of the area is inefficient. Therefore, attention must be paid both to the effective specific surface area and to its ratio in the total specific surface area.

Biofilm amount attached to carrier surface and biofilm stability vary depending on surface properties, wastewater characteristics and reactor operation conditions (Piculell, Maria, 2016). Generally, biofilm is fragile during its first attachment to a surface, and consequently, peeling-type biofilm ruptures (as a whole) can be experienced and the reactor efficiency can be affected negatively (Hu et al., 2017). The attachment stage, which is the first stage of biofilm formation, has a decisive effect on the adhesion and structure of biofilm in later stages (Busscher & Van Der Mei, 1995).

There are limited number of studies on the effect of carrier element geometry on removal efficiency. In one of these studies, it is reported that the material length and biofilm thickness of a carrier element are effective on inhibition exposure, and a biofilm on short carriers is more exposed to inhibition (Garcia, 2015).

Generally, microorganisms have a negative surface charge, so they tend to attach more easily to positively charged surfaces. In a recent study, it is shown that modification of the surface of the carrier element (high density polyethylene, HDPE) with positively charged polymers (polyquaternium-10, PQAS-10, and cationic polyacrylamides, CPAM) shortens the biofilm attachment time and provides biofilm enrichment (Mao et al., 2017). Besides, surface properties such as surface roughness, hydrophobicity of the surface and surface energy are also among the factors affecting microbial attachment. Microorganisms tend to adhere preferably to hydrophobic surfaces (Rosenberg and Kjelleberg 1986; Donlan, 2002; Thomas et al., 2004; Harmsen et al., 2010). Accordingly, surface modification can be an attractive option to control biofilm formation. By accelerating biofilm attachment, the long acclimation time, which makes it difficult to start biofilm systems especially in cold regions, can be shortened (Hu et al., 2017). Also, with the stability of the attached biofilm, peeling-type ruptures can be prevented, the treatment efficiency can be stabilized and even, the amount of carrier element needed can be reduced. Currently, there is no method employed to accelerate biofilm formation and/or to increase biofilm stability on the surface of the carrier element used in wastewater treatment plants. Considering the capacities of wastewater treatment plants, the economical and easy application of the method to be developed is highly important owing to the possibilities in transferring the invention to industry and practice.

SUMMARY

Within the scope of this invention, carrier materials with large surface areas that can be used in wastewater treatment plants and a surface modification method have been developed to accelerate the formation of a biofilm layer on the surfaces of these carrier materials and/or to increase the biofilm layer stability. In existing carrier elements, the effective specific surface area and the ratio of this area to the total specific surface area are small. Consequently, the inefficient surface area in total area is high, and creating a large surface area requires the use of large amounts of carrier elements.

The carrier element developed within the scope of the invention is designed in both cubic (1) and cylindrical (2) forms, and the effective specific surface areas of the carrier element are increased in the both structures. The effective specific surface area of the cylindrical carrier element (2) is approximately 1.3-1.5 times greater than that of similar cylindrical carriers in the same dimensions. At the same time, the ratio of effective specific surface area to total specific surface area is high, and the carrier is efficient in terms of area usage. The configuration with the highest ratio of effective specific surface area to total specific surface area is the cubic configuration (1). In the cubic configuration (1), the ratio of effective specific surface area to total specific surface area is about 20% higher than the ratio in the cylindrical configuration (2) with the same dimensions. The high figures of effective specific surface areas and the low figures of inefficient areas can help to reduce the amount of carrier to be used in the reactor. In addition, this indirectly results in improved mixing conditions in the reactor and consequently a better mass transfer.

In existing carrier elements with high surface area, biofilm growth chambers are very small and these chambers get blocked, especially in particle-intensive wastewater applications. In all designs of the carrier element developed within the scope of the invention, in addition to two-way open single-channel biofilm growth chambers (9), there are three-way open channels (5, 6). These three-way open channels (5, 6) are of a nature that contributes to the prevention of particle-induced blockages in all cylindrical (2) and cubic (1) designs of the invention. These channels provide advantages in terms of blockage and material transfer especially in the second-stage plate-type cylindrical configuration with increased surface area and reduced chamber clearance, and in the cylindrical configuration to be produced in small diameters.

The thickness and amount of biomass attaching to the surface of existing carrier elements, is limited. The cylindrical configuration (2) of the carrier element developed within the scope of the invention provides protected inner surfaces and supports biofilm development. The improvement of biofilm development contributes to the protection of microorganisms on the inner surface and to their resistance to inhibition. This is an advantage for industrial wastewater treatment plants, where a wide variety of pollutants are generated and a change of wastewater characteristics are relatively much, and/or for urban wastewater treatment plants with large industrial inputs. In addition, thanks to the protected surfaces, partial anoxic and/or anoxic conditions may form in the interior of the biofilm, which could cause concurrent development of nitrification/denitrification and contribute to nitrogen removal.

In systems employing existing carrier elements, material and oxygen transfer into the biofilm is prevented and consequently energy consumption increases. The cubic configuration (1) of the carrier element developed within the scope of this invention can allow the biofilm surface to be open to water and air movements and thus contribute to the improvement of oxygen and material transfer into the biofilm. With the improvement of material and oxygen transfer, the electricity and energy consumption for ventilation is reduced. The cubic configuration may be further advantageous, especially in wastewaters where the change in characteristics is less and inhibition effects are not observed.

In biofilm-based wastewater treatment systems, in addition to the carrier element design, the prolonged biofilm formation on the carrier element surface and consequently very long start-up period of the plant, especially in cold climates, also reduce the efficiency of the process. Moreover, even though the biofilm structure varies depending on the wastewater properties, ambient conditions and reactor operating conditions, the first biofilm formation on existing carrier element surfaces can be fragile and peeling-type biofilm ruptures (as a whole) can be experienced. In this case, the reactor start-up period is prolonged and the treatment performance fluctuates. With the surface modification method developed within the scope of this invention, biofilm attachment to the surface takes place more effectively allowing a quick biofilm development; thus, the plant start-up period is significantly shortened. Owing to the surface process developed, the fragility of the attached biofilm is reduced, the peeling-type biofilm ruptures (as a whole) are prevented, and consequently, the treatment process performance is made more stable. Also, along with the decrease in biofilm fragility, the biofilm thickness is increased which makes it possible to protect the microorganisms in the interior of the biofilm and to make the biofilm more resistant against inhibition. The concurrent development of nitrification/denitrification in the interior of the biofilm may contribute to a more effective nitrogen removal.

BRIEF DESCRIPTION OF THE SEVERAL VIEWS OF THE DRAWING(S)

FIG. 1: Perspective view of the cubic configuration of the carrier element

Figure 2:
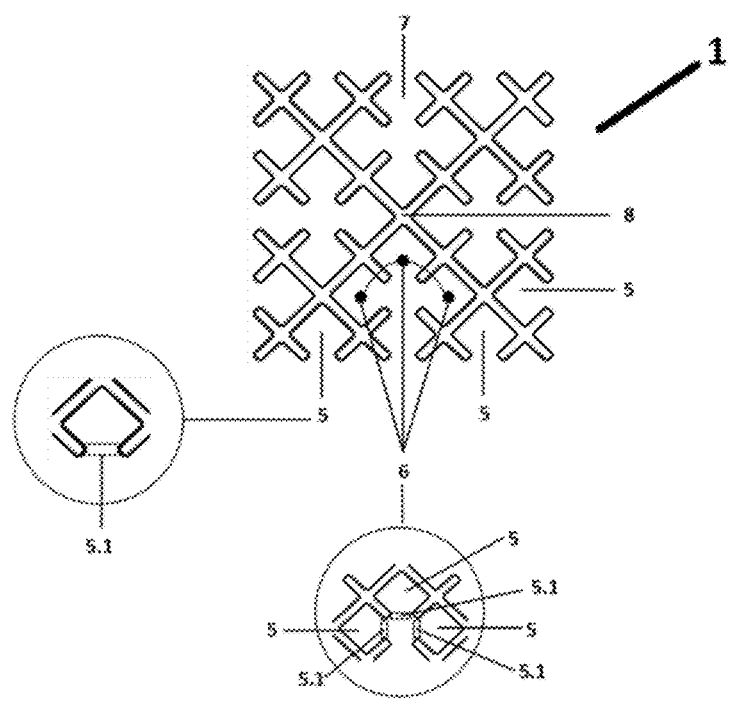

FIG. 2: Top view of the cubic configuration of the carrier element

Figure 3:
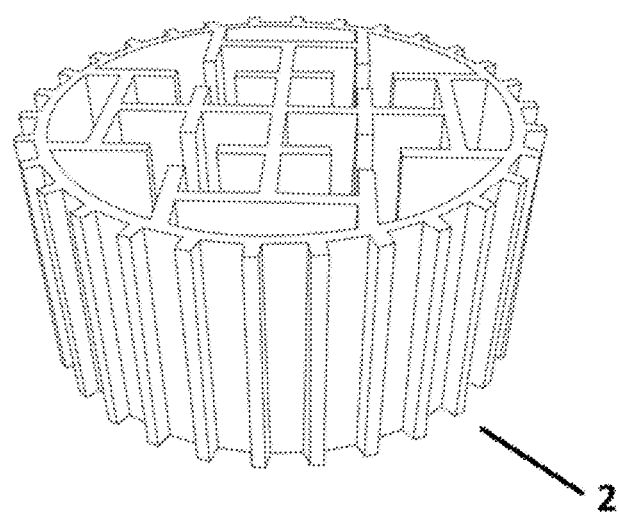

FIG. 3: Perspective view of the cylindrical configuration of the carrier element FIG. 4: Top view of the cylindrical configuration of the carrier element FIG. 5: Perspective view of the second-stage plate-type cylindrical configuration of the carrier element FIG. 6: Top view of the second-stage plate-type cylindrical configuration of the carrier element FIG. 7: Flow chart of the surface modification process

DESCRIPTIONS OF THE REFERENCES IN THE FIGURES

1: Cubic configuration of the carrier element
2: Cylindrical configuration of the carrier element
3: Second-stage plate-type cylindrical configuration of the carrier element
4: Surface modification process
5: Three-way single-channel biofilm growth chamber
5.1: Channel
6: Interlocking three-way three-channel biofilm growth chamber
7: Interlocking four-way two-channel biofilm growth chamber
8: Central support section
9: Two-way biofilm growth chamber
10: Interlocking three-way four-channel biofilm growth chamber
11: Circular outer surface
12: Fin
A: Paraffin wax
B: Paraffin liquefaction step
C: Carrier element
D: Step of immersing the carrier element into paraffin
E: Step of removing excess paraffin
F: Drying step
G: Step of immersing into peptone solution

DETAILED DESCRIPTION

The invention relates to (i) the development of a carrier element providing high surface area for biofilm formation in wastewater treatment plants and (ii) a carrier element surface modification method for accelerating and enriching biofilm formation.

Within the scope of the invention, carrier elements—with a large effective specific surface area and with a high ratio of this area to total specific surface area—have been developed. Depending on the designs of these carrier elements, the representation of the biofilm growth chamber is shown in (9). When the carrier element is placed in a reactor with circulating wastewater, a biofilm is formed in this chamber (9) by microorganisms. The geometric form of the biofilm growth chamber (9) may vary depending on the carrier element design. Since the liquid flow in this biofilm growth chamber (9) is through the upper and lower clearances, this design (9) is called two-way biofilm growth chamber. Three-way single-channel biofilm growth chambers (5) allow liquid flow in three directions, which are through the upper and lower clearances and the channel (5.1). Interlocking three-way three-channel biofilm growth chamber (6) includes three combined three-way three-channel biofilm growth chambers (5). The interior parts of these chambers (5) allow liquid transfer among each other. The four-way two-channel biofilm growth chamber (7) allows interlocking liquid transfer in four directions, which are through the upper and lower clearances and the two channels (5.1). Interlocking three-way four-channel biofilm growth chamber (10) has four channels (5.1) and four three-way single-channel biofilm growth chambers (5).

Based on the cubic configuration (1) that allows increased oxygen transfer and multi-directional substance transfer on biofilm surface and that has in its central support section (8) three-way single-channel biofilm growth chambers (5), interlocking three-way three-channel biofilm growth chambers (6) and interlocking four-way two-channel biofilm growth chambers (7), a cylindrical configuration (2) has been developed to contribute to the increase of biofilm thickness and to allow a protected and inhibition-resistant biofilm growth, with a central support section (8) surrounded by three-way single-channel biofilm growth chambers (5), two-way biofilm growth chambers (9) and interlocking three-way four-channel biofilm growth chambers (10), having a circular outer surface (11) and fins (12) with the same height as the circular outer surface (11). Carrier elements can be made of polyethylene (PE), high density polyethylene (HDPE), polypropylene (PP), polyvinylchloride (PVC) and/or composite plastic materials. The specific gravity of the material is preferably in the range between 0.94 and 1.05 g/cm$^3$. The carrier elements can be made from pure raw material and/or preferably, owing to environment-friendly nature, from duly recycled material that is not contaminated with micro-pollutants and/or toxic substances. While the protected cylindrical carrier element configuration (2) with increased biofilm thickness compared to the cubic configuration (1) allows more biomass retention, the cubic configuration (1), on the other hand, allows material transfer into the biofilm to take place from three or four directions owing to water movements, as well as allowing relatively thinner biofilm formation due to shear forces and supporting more oxygen and substance transfer into the biofilm compared to the cylindrical configuration (2).

The effective specific surface area in the invention is in a range of 490-960 m$^2$/m$^3$ in the cubic configuration (1), 430-850 m$^2$/m$^3$ in the cylindrical configuration (2) and 410-680 m$^2$/m$^3$ in the second-stage plate-type cylindrical configuration (3). The ratio of effective specific surface area to total specific surface area is averagely 97% in the cubic configuration (1), 76% in the cylindrical configuration (2) and 71% in the second-stage plate-type cylindrical configuration (3).

The cubic configuration (1) of the carrier element to be used for biofilm development as a part of the present invention is shown in FIG. 1 and FIG. 2. The carrier element (1) is composed of, firstly, three-way single-channel biofilm growth chambers (5) for increasing substance transfer to biofilm and supporting biofilm renewal owing to shear forces, interlocking three-way three-channel biofilm growth chambers (6), interlocking four-way two-channel biofilm growth chambers (7) and a central support section (8). The outer surface of the carrier element contains recesses contributing to the rotational movements of the carrier in water and reducing the inefficient area on the outer surface which is unusable due to friction. The cubic carrier element (1) may preferably have a width of 15-30 mm and a height of 15-30 mm, i.e. an edge of it may preferably be 15-30 mm long. The diagonal clearance may be preferably 3-7.3 mm in three-way single-channel biofilm growth chamber (5) and preferably 6.7-14.7 mm in three-way three-channel biofilm growth chamber (6). These parameters may vary depending on production technology.

Figure 4:
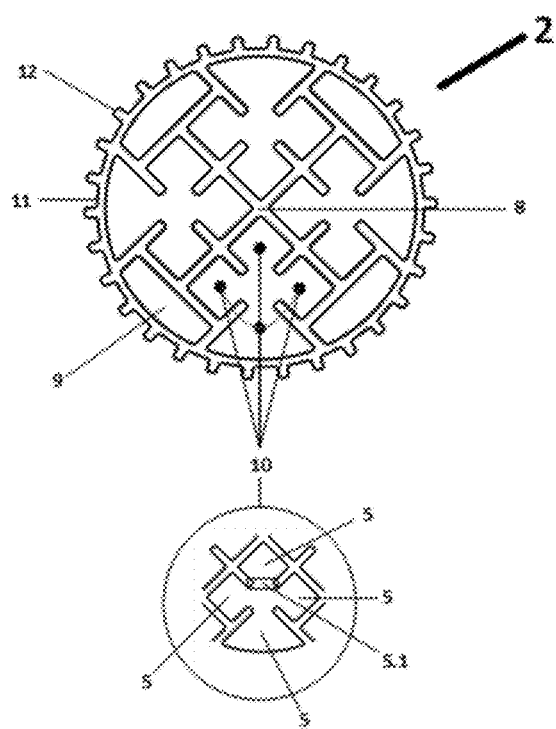

The cylindrical configuration (2) of the carrier element to be used for biofilm development as a part of the present invention is shown in FIG. 3 and FIG. 4. The cylindrical configuration (2) has a central support section (8) surrounded by two-way biofilm growth chambers (9), interlocking three-way four-channel biofilm growth chambers (10), a circular outer surface (11) and fins (12). The outer surface (11) of the cylindrical form carrier element (2) contains small fins (12) contributing to the rotational movements of the carrier in water and reducing the inefficient area on the outer surface which is unusable due to friction. The cylindrical carrier element (2) may preferably have a diameter of 15-30 mm and a height of 5-15 mm, and may contain preferably equally-spaced 30 to 60 fins (12) in 0.7-1.5 mm height. The highest diagonal clearance in the interlocking three-way four-channel biofilm growth chamber (10) may preferably be 6.7-14.7 mm.

Figure 5:
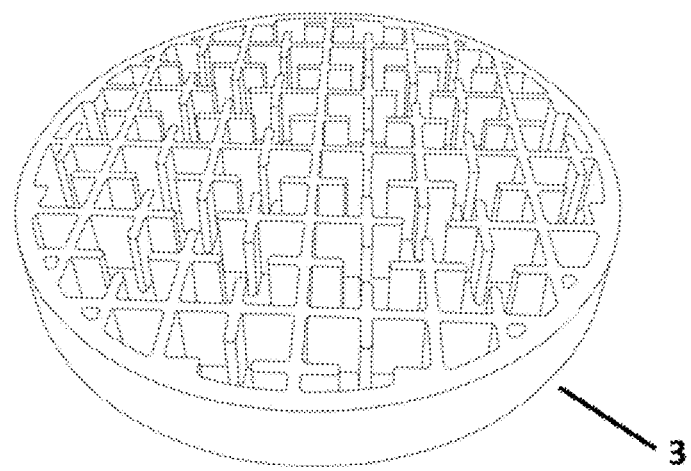
Figure 6:
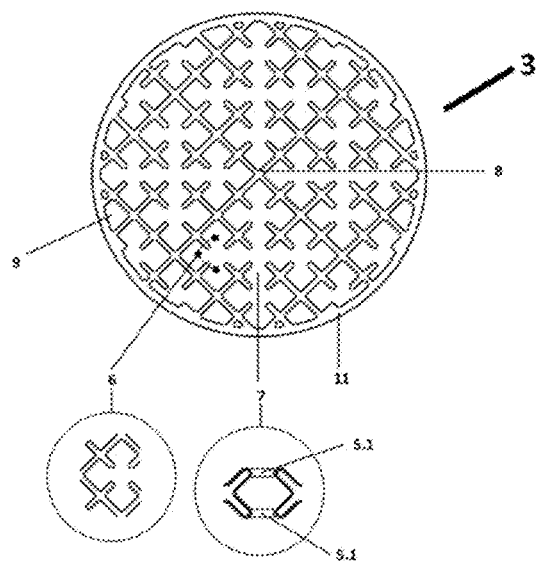
Figure 7:
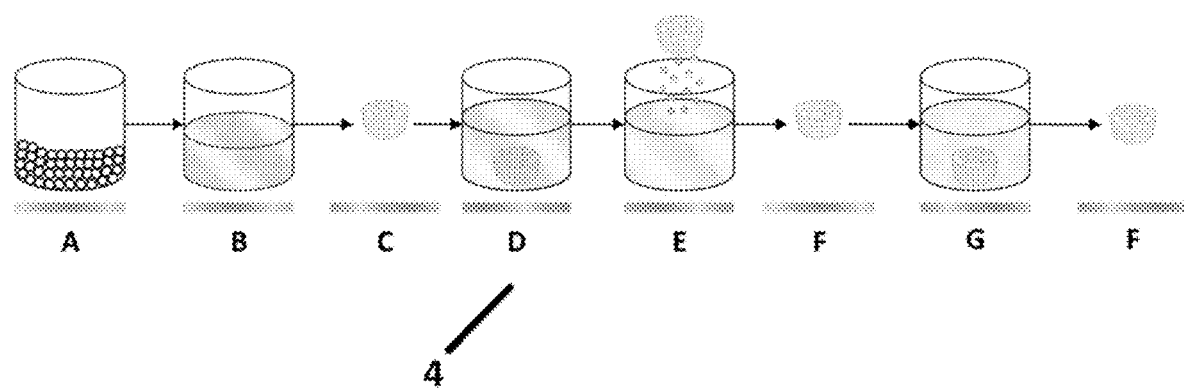

The second-stage plate-type cylindrical configuration (3) of the carrier element to be used for biofilm development as a part of the present invention is shown in FIG. 5 and FIG. 6. The plate-type cylindrical configuration (3) has a central support section (8) surrounded by two-way biofilm growth chambers (9), interlocking three-way three-channel biofilm growth chambers (6), interlocking four-way two-channel biofilm growth chambers (7) and a circular outer surface (11). Unlike the configuration in FIG. 3, the number of biofilm growth chambers is increased. The second-stage plate-type cylindrical carrier (3) may have a diameter in the range of 30-50 mm and a height of 2-5 mm. The plate-type carrier element (3) may have a larger diameter than the cylindrical carrier (2), which is a part of the invention. This provides an advantage by retaining the carrier element in the reactor, allowing the use of a grille/sieve system with larger pores.

The carrier elements can preferably be produced by extrusion and/or injection molding methods.

The carrier element surface modification method (4), which is another subject matter of the invention, is related to the acceleration of biofilm attachment to the surface and the reduction of biofilm fragility. In many studies, it is reported that microorganism attachment to a surface is directly related to the hydrophobicity of the surface and that the hydrophobicity supports the microorganism attachment to the surface (Donlan et al., 2002; Cerca et al., 2005; Mazumder et al., 2010; Pagedar et al., 2010).

Accordingly, the invention relates to increasing the hydrophobicity of the carrier element surface used in wastewater treatment plants by coating it with paraffin wax, consequently, shortening the biofilm formation time, and also reducing the biofilm fragility and preventing peeling-type complete biofilm ruptures, owing to the achievement of a more stable and durable structure in the attached biofilm. In the surface modification method (4) developed within the scope of the invention, the carrier element surface is washed with water, freed from particles like dust, burr, etc., dried at room temperature and made ready for surface treatment. Paraffin wax (A) in solid state at room temperature containing 25-50 carbon atoms per molecule is switched to liquid state (B) at a temperature of 70-80° C. by using hot water bath, oven, etc. The carrier element (C) is immersed into the bath containing hot paraffin wax in liquid state (D); after a period of time (preferably a few seconds), the material is removed from the bath, and the excess paraffin remaining on the surface is allowed to flow away and harden (E). Finally, the material is allowed to dry at room temperature (F). Drying process is preferably realized by keeping the material at room temperature for 5-10 seconds.

The carrier element surface modification method (4) of the invention also includes the impregnation of a nutrient solution on the carrier element surface covered with paraffin wax as a second stage surface treatment in order to support the acceleration of biofilm formation in nutrient-poor wastewater. For this purpose, the carrier element coated with paraffin is immersed in the nutrient solution (G) and after an average of 24 hours, it is removed from the solution and allowed to dry at room temperature (F). In an embodiment of the invention, it is possible to use peptone solution as the nutrient. For this purpose, the carrier element coated with paraffin is immersed into a solution preferably containing 20-30% peptone by weight, and the described process is performed.

Surface treatment can be applied either completely on the all carrier elements added to the reactor, or partially.

In wastewaters with quite variable characteristics, especially in industrial wastewaters, trace elements (such as zinc, copper, cobalt, molybdenum) required for biological reactions may be insufficient. In wastewaters without sufficient trace elements, the needed elements can be determined by analyzing the wastewater, and can be applied to the carrier material surface preferably by adding an appropriate amount of relevant trace elements in powder form into the melted paraffin (B) or by immersing into a solution of trace elements.

INDUSTRIAL APPLICATION OF THE INVENTION

The carrier material developed, can be produced by plants processing plastic materials by injection and/or extrusion method.

The carrier material surface modification method developed, can be applied by enterprises having infrastructures for coating by immersion method.

REFERENCES

Rosenberg, M. and Kjelleberg, S. (1986). Hydrophobic interactions in bacterial adhesion. Advances in Microbial Ecology 9, 353-393.

Donlan, R. M. (2002). Biofilms: microbial life on surfaces. Emerging Infectious Diseases 8(9), 881-890.

Thomas, W. E., Nilsson, L. M., Forero, M., Sokurenko, E. V. and Vogel, V. (2004). Shear-dependent 'stick-and-roll' adhesion of type 1 fimbriated *Escherichia coli*. Molecular Microbiology 53, 1545-1557.

Harmsen, M., Yang, L., Pamp, S. J. and Tolker-Nielsen, T. (2010). An update on *Pseudomonas aeruginosa* biofilm formation, tolerance, and dispersal. FEMS Immunology and Medical Microbiology 59, 253-268.

Piculell, Maria, (2016). New Dimensions of Moving Bed Biofilm Carriers: Influence of biofilm thickness and control possibilities. Lund: Department of Chemical Engineering, Lund University Garcia, Kody, The Effect of Biofilm Carrier Length on Nitrification in Moving Bed Biofilm Reactors: An Examination of Mixing Intensity, Shock Loadings, and pH Changes (2016). http://digitalrepository.unm.edu/ce_etds/115

Young, B., Delatolla, R., Kennedy, K., Laflamme, E., Stintzi, A., (2017). "Low temperature MBBR nitrification: Microbiome analysis" Water Res., 111, 224-233.

Huang, C., Shi, Y., Xue, J., Zhang, Y., Gamal El-Din, M., Liu, Y., (2017). "Comparison of biomass from integrated fixed-film activated sludge (IFAS), moving bed biofilm reactor (MBBR) and membrane bioreactor (MBR) treating recalcitrant organics: Importance of attached biomass" J. Hazard. Mater., 326, 120-129.

Mannina, G., Capodici, M., Cosenza, A., Cinã, P., Di Trapani, D., Puglia, A. M., Ekama, G. A., (2017). "Bacterial community structure and removal performances in IFAS-MBRs: A pilot plant case study" J. Environ. Manage., 198, 122-131.

Cerca, N., Pier, G. B., Vilanova, M., Oliveira, R., Azeredo, J., (2005). "Quantitative analysis of adhesion and biofilm formation on hydrophilic and hydrophobic surfaces of clinical isolates of *Staphylococcus epidermidis*" Res. Microbiol., 156, 506-514.

Mazumder, S., Falkinham, J. O., Dietrich, A. M., Puri, I. K., Falkinham Iii, J. O., (2010). Role of hydrophobicity in bacterial adherence to carbon nanostructures and biofilm formation" J. Bioadhesion Biofilm Res., 26, (3): 333-339.

Pagedar, A., Singh, J., Batish, V. K., (2010). "*Staphylococcus aureus* biofilms and temperature influences its survival in preformed biofilms Introduction *" S98 J. Basic Microbiol., 50, 98-106.

Barwal, A., & Chaudhary, R. (2015). Impact of carrier filling ratio on oxygen uptake and transfer rate, volumetric oxygen transfer coefficient and energy saving potential in a lab-scale MBBR. Journal of Water Process Engineering, 8, 202-208. https://doi.org/10.1016/J.JWPE.2015.10.008

Busscher, H. J., & Van Der Mei, R. B. H. C. (1995). Initial microbial adhesion is a determinant for the strength of biofilm adhesion. FEMS Microbiology Letters, 128(3), 229-234. https://doi.org/10.1016/0378-1097(95)00103-C Gu, Q., Sun, T., Wu, G., Li, M., & Qiu, W. (2014). Influence of carrier filling ratio on the performance of moving bed biofilm reactor in treating coking wastewater. Bioresource Technology, 166, 72-78. https://doi.org/10.1016/J.BIORTECH.2014.05.026

Hu, H., He, J., Yu, H., Liu, J., & Zhang, J. (2017). A strategy to speed up formation and strengthen activity of biofilms at low temperature. RSC Advances, 7(37), 22788-22796. https://doi.org/10.1039/c7ra02223a Jing, J. Y., Feng, J., & Li, W. Y. (2009). Carrier effects on oxygen mass transfer behavior in a moving-bed biofilm reactor. Asia-Pacific Journal of Chemical Engineering, 4(5), 618-623. https://doi.org/10.1002/apj.302

Mao, Y., Quan, X., Zhao, H., Zhang, Y., Chen, S., Liu, T., & Quan, W. (2017). Accelerated startup of moving bed biofilm process with novel electrophilic suspended biofilm carriers. Chemical Engineering Journal, 315, 364-372. https://doi.org/10.1016/J.CEJ.2017.01.041

The invention claimed is:

1. A surface modification method of a carrier element developed for use of microorganisms growing on biofilm, for wastewater treatment and pollutant removal, characterized by comprising the following steps of:
   Washing a carrier element to free it from contaminants,
   Liquefaction of a paraffin wax containing trace elements,
   Immersion of the carrier element into the paraffin wax bath for 3-5 seconds,
   Allowing the excess paraffin remaining on the carrier element surface to flow away and harden for 3-5 seconds,
   Allowing the material to dry at room temperature for 5-10 seconds.

2. A surface modification method according to claim 1, characterized in that paraffin-modified surface of the carrier element is impregnated with nutrients and trace elements.

3. A surface modification method according to claim 2, characterized in that the impregnation with the nutrients comprises immersion of the paraffin-modified surface of the carrier element into a nutrient solution and keeping it there for 24 hours.

4. A surface modification method according to claim 3, characterized in that the nutrient solution is a solution containing 20-30% peptone by weight.

5. A surface modification method according to claim 1, wherein the carrier element is selected from the group consisting of
   a cubic form carrier element (1),
   a cylindrical form carrier element (2) and,
   a second-stage plate-type carrier element (3), wherein
   wherein the cubic form carrier element (1) comprises:
   a central support section (8)
   three-way single biofilm growth chambers (5),
   three-way three biofilm growth chambers (6) and
   four-way two biofilm growth chambers (7),
   wherein the cylindrical form carrier element (2) comprises:
   a central support section (8)
   two-way biofilm growth chambers (9),
   three-way four biofilm growth chambers (10),
   a circular outer surface (11), and fins (12) of the same length as the outer surface height,
   wherein second-stage plate-type carrier element (3) comprises:
   a central support section (8),
   three-way three biofilm growth chambers (6),
   two-way biofilm growth chamber (9),
   four-way two biofilm growth chambers (7) and
   a circular outer surface (11).

6. A surface modification method according to claim 1, further comprising adding trace elements in powder form into the melted paraffin wax or immersing the carrier element coated with paraffin wax into a solution of trace elements.

* * * * *